(12) United States Patent
Bontus et al.

(10) Patent No.: US 8,437,524 B2
(45) Date of Patent: May 7, 2013

(54) IMAGING SYSTEM FOR IMAGING A REGION OF INTEREST IN DIFFERENT PHASES

(75) Inventors: Claas Bontus, Hamburg (DE); Michael Grass, Buchholz in der Norheide (DE); Carsten Oliver Schirra, London (GB); Udo Van Stevendaal, Ahrensburg (DE); Guy Lavi, Avichail (IL)

(73) Assignee: Koninklijke Philips Electronics N. V., Eindhoven (NL)

( * ) Notice: Subject to any disclaimer, the term of this patent is extended or adjusted under 35 U.S.C. 154(b) by 972 days.

(21) Appl. No.: 12/521,899

(22) PCT Filed: Jan. 2, 2008

(86) PCT No.: PCT/IB2008/050002
§ 371 (c)(1),
(2), (4) Date: Jul. 1, 2009

(87) PCT Pub. No.: WO2008/084413
PCT Pub. Date: Jul. 17, 2008

(65) Prior Publication Data
US 2009/0310825 A1    Dec. 17, 2009

(30) Foreign Application Priority Data
Jan. 8, 2007 (EP) .................................. 07100235

(51) Int. Cl.
*G06K 9/00* (2006.01)
(52) U.S. Cl.
USPC ......................................................... 382/131
(58) Field of Classification Search .................. None
See application file for complete search history.

(56) References Cited

U.S. PATENT DOCUMENTS

| | | | |
|---|---|---|---|
| 6,597,803 B1 * | 7/2003 | Pan et al. ....................... | 382/131 |
| 7,415,093 B2 * | 8/2008 | Tkaczyk et al. ................. | 378/8 |
| 2004/0136490 A1 | 7/2004 | Edic et al. | |
| 2007/0036418 A1 * | 2/2007 | Pan et al. ....................... | 382/131 |
| 2008/0086052 A1 * | 4/2008 | Hsieh ............................. | 600/427 |
| 2009/0141935 A1 * | 6/2009 | Grass et al. .................... | 382/103 |
| 2009/0310825 A1 * | 12/2009 | Bontus et al. ................. | 382/107 |
| 2011/0176710 A1 * | 7/2011 | Mattiuzzi et al. ............. | 382/128 |

OTHER PUBLICATIONS

Koken, P., et al.; Aperture Weighted Cardiac Cone-beam Reconstruction using Retrospective ECG Gating; 2006; Phys. Med. Biol.;51:3433-3448.
Manzke, R., et al.; Automatic phase determination for retrospectively gated cardiac CT; 2004; Med. Phys.;31(12) 3345-3362.

(Continued)

*Primary Examiner* — Bhavesh Mehta
*Assistant Examiner* — Tahmina Ansari

(57) ABSTRACT

The invention relates to an imaging system for imaging a region of interest comprising a moving object, which moves less in small motion phases than in large motion phases. Detection values are provided and a small motion determination unit (15) determines the motion of the object in the region of interest in the small motion phases from the 5 detection values. A large motion determination unit (16) determines the motion of the object in the large motion phases from the determined motion of the object in the small motion phases. A reconstruction unit (17) reconstructs an image of the region of interest from the detection values, wherein the reconstruction unit (17) is adapted for performing a motion compensation using the determined motions in the small and large motion phases.

20 Claims, 8 Drawing Sheets

OTHER PUBLICATIONS

Taguchi, K., et al.; Toward time resolved 4D cardiac CT imaging with patient dose reduction: estimating the global heart motion; 2006; Physics of Medical Imaging; vol. 6142.

Taguchi, K., et al.; Toward time resolved cardiac CT images with patient dose reduction: Image-based motion estimation; 2006; IEEE Trans. on Nuclear Science; pp. 2029-2032.

Van Straten, M., et al.; Removal of arterial wall calcifications in CT angiography by local subtraction; 2003; Medical Physics; 30(5)761-770.

Schaefer, D., et al.; Motion-Compensated and Gated Cone Beam Filtered Back-Projection from 3-D Rotational X-Ray Angiography; 2006; IEEE Trans. on Medical Imaging; 25(7)898-906.

* cited by examiner

IMAGING SYSTEM FOR IMAGING A REGION OF INTEREST IN DIFFERENT PHASES

FIELD OF THE INVENTION

The present invention relates to an imaging system, an imaging method and a computer program for imaging a region of interest comprising a moving object. The present invention relates further to a motion determination system, a motion determination method and a computer program for determining the motion of a moving object in a region of interest, and the present invention further relates to an imaging system, an imaging method and a computer program for imaging a contrast agent within a moving object in a region of interest.

BACKGROUND OF THE INVENTION

An imaging system for imaging a region of interest comprising a moving object is, for example, a computed tomography system for imaging a heart of a patient. Such a computed tomography system is generally be referred to as cardiac CT system. The cardiac CT system comprises an electrocardiograph for determining phase positions of the heart, wherein for a reconstruction of a region of interest of the heart only detection values are used, which have been acquired at certain phase positions of the heart, at which the heart is in a relative rest condition. Thus, only a part of the detection values is used for reconstructing a region of interest of the heart. This reduces the signal-to-noise ratio and decreases, therefore, the image quality.

SUMMARY OF THE INVENTION

It is therefore an object of the invention to provide an imaging system, an imaging method and a computer program for imaging a region of interest comprising a moving object, which moves less in small motion phases than in large motion phases, which reconstruct an image of the region of interest having an improved image quality.

In a first aspect of the present invention an imaging system for imaging a region of interest comprising a moving object, which move less in small motion phases than in large motion phases, is presented, wherein the imaging system comprises:
  a detection values provision unit for providing detection values, which depend on properties of the moving object,
  a small motion determination unit for determining the motion of the object in the region of interest in the small motion phases from the detection values,
  a large motion determination unit for determining the motion of the object in the region of interest in the large motion phases from the determined motion of the object in the small motion phases,
  a reconstruction unit for reconstructing an image of the region of interest from the detection values, wherein the reconstruction unit is adapted for performing a motion compensation using the determined motions in the small and large motion phases.

The invention is based on the idea that, since the motion in the small and in the large motion phases is used for performing a motion compensation during the reconstruction of the region of interest, also detection values corresponding to large motion phases of the object can be used for reconstructing the region of interest. This increases the signal-to-noise ratio of the reconstructed image and improves, therefore, the quality of the reconstructed image.

Small motion phases are motion phases in which the object moves only a little or not at all or less than in the large motion phases. For example, if the object is a heart, the small motion phase is a phase of relative rest of the heart, and a large motion phase is a phase of stronger motion of the heart.

Preferentially the small motion determination unit is adapted for
  reconstructing images of the region of interest at several phase positions within the small motion phases from the detection values,
  determining the motion of the object in the region of interest in the small motion phases by comparing the images of the region of interest at the several phase positions. This allows determining the motion of the object in the region of interest and the small motion phases with a high reliability.

It is further preferred that the small motion determination unit is adapted for
  determining the motion between one phase position to another phase position by determining a similarity transformation such that a transformed image at the one phase position, to which the similarity transformation has been applied, is similar to the image at the other phase position with respect to a given similarity measure,
  determining at least between two of the several phase points within a small motion phase at least one similarity transformation, wherein the at least one similarity transformation defines the motion within the small motion phase.

The similarity transformation, is, for example, a transformation including a rotation, a translation and a scaling of structures, which are detectable in the image of the region of interest at the several phase points. The similarity transformation is preferentially a nine-parametric affine transformation. The similarity measure is, for example, a correlation or a sum of absolute differences. Preferentially, a transformed image is similar to another image, if the similarity measure yields a similarity value smaller than a predetermined similarity threshold. In addition or alternatively, two images are preferentially similar, if the similarity measure applied to the two images yields a minimal similarity value. Preferentially, the similarity transformation is not applied to the whole image, but only to structures, which can be identified in both images. This allows improving the determination of the motion and, therefore, improving the quality of a reconstructed image, which uses the determined motion for motion compensation.

It is further preferred that the small motion determination unit is adapted for determining a similarity transformation between an image at one phase position and an image at another phase position by firstly determining a translation such that an image, to which the translation has been applied, at the one phase position is similar to the image at the other phase position with respect to the given similarity measure, wherein the determined translation is used as initial similarity transformation for the determination of the similarity transformation. This gives a good first guess for the similarity transformation which has to be determined, accelerates the determination and reduces the computational costs for determining the similarity transformation and, thus, of the determination of the motion and of the reconstruction of an image of the region of interest.

In the region of interest, the object can comprise at least one high density element having a density within a given density range. In this case, the small motion determination unit is preferentially adapted for determining the motion between one phase position to another phase position by determining a similarity transformation such that a transformed at least one high density element, which is the at least high density element in the image at the one phase position, to which the similarity transformation has been applied, is similar to the at least one high density element in the image at the other phase position with respect to a given similarity measure, determining at least between two of the several phase points within a small motion phase at least one similarity transformation, wherein the at least one similarity transformation defines the motion within the small motion phase. The high density elements are, for example, calcifications preferentially in a heart of a patient. Furthermore, if the imaging system is a computed tomography system, the density of the calcifications is preferentially in the range of 100 to 160 Houndfields units (HU), further preferred in the range of 120 to 140 HU, and it is further preferred that the density of the calcifications is 130 HU. Preferred densities of the at least one high density element are further disclosed in "Quantification of coronary artery calcium using ultrafast computed tomography", Agatston et al., J. Am Coll Cardiol 15 (4) pp. 827-832, 1990, which is herewith incorporated by reference.

Since the at least one high density element can easily be identified in the different images, the accuracy of the determination of the similarity transformation and, therefore, of the motion is further improved. Furthermore, if the at least one high density element is a calcification of a heart of a patient, the dimensions and the shape of the calcification can be determined from the reconstructed image, which has been reconstructed using motion compensation and, therefore, a calcium scoring can be preformed with high reliability. If the heart comprises more than one calcification, for each calcification the motion can be determined independently from the motion of the other calcifications, and each calcification can be reconstructed motion compensated, wherein for each calcification the respective motion is used. This allows determining the dimensions and the shape of different calcifications, even if different calcification move differently, for example, because there are located at different location within the heart of a patient.

It is further preferred that the small motion determination unit is adapted for determining a similarity transformation between the at least one high density element in an image at one phase position and the at least one high density element in an image at another phase position by firstly determining a translation such that a translated at least one high density element, which is the at least high density element in the image at the one phase position, to which the translation has been applied, is similar to the at least one high density element in the image at the other phase position with respect to the given similarity measure, wherein the determined translation is used as initial similarity transformation for the determination of the similarity transformation. This translation is a good first guess for the desired similarity transformation, wherein the determination of the similarity transformation is accelerated and wherein the computational costs required for determining the similarity transformation are reduced.

It is preferred that the large motion determination unit is adapted for determining the motion of the object in the region of interest in a large motion phase by interpolating between determined motions of small motion phases, which are adjacent to the large motion phase. The determination of the motion of the object in a large motion phase by interpolation allows determining this motion with low computational costs and high reliability.

The detection values provision unit is preferentially a detection values generation unit for generating detection values which depend on properties of the moving object. It is further preferred that the detection values generation unit is a combination of an X-ray source, an X-ray detection unit and a moving unit for moving the X-ray source with respect to the region of interest, i.e. the imaging system is preferentially a computed tomography system comprising at least the units defined in claim 1.

In a further aspect of the invention a motion determination system for determining the motion of a moving object, which moves less in small motion phases than in large motion phases, in a region of interest, is presented, wherein the motion determination system being provided with detection values, which depend on properties of the moving object, provided by a detection value provision unit, wherein the motion determination system comprises a small motion determination unit for determining the motion of the object in the region of interest in the small motion phases from the detection values, a large motion determination unit for determining the motion of the object in the region of interest in the large motion phases from the determined motion of the object in the small motion phases. The motion determination system preferentially further comprising a reconstruction unit for reconstructing an image of the region of interest from the detection values, wherein the reconstruction unit is adapted for performing a motion compensation using the determined motions in the small and large motion phases.

In a further aspect of the invention an imaging system for imaging a contrast agent within a moving object is presented, wherein the moving object comprises at least one high density element having a density within a given range of density in the region of interest and wherein the moving object moves less in small motion phases than in large motion phases, wherein the imaging system comprises:

a detection values provision unit for providing first detection values, which depend on properties of the moving object, if the contrast agent is not present within the object, a small motion determination unit for determining the motion of the object in the region of interest in the small motion phases from the first detection values, a large motion determination unit for determining the motion of the object in the region of interest in the large motion phases from the determined motion of the object in the small motion phases, a reconstruction unit for reconstructing a first image of the region of interest comprising the object comprising the at least one high density element from the first detection values, wherein the reconstruction unit is adapted for performing a motion compensation using the determined motions in the small and large motion phases, wherein the detection values provision unit is further adapted for providing second detection values, which depend on properties of at least one of the moving object and the contrast agent, if the contrast agent is present within the object, and wherein the reconstruction unit is further adapted for reconstructing a second image of the region of interest comprising the object from the second detection values,
wherein the imaging system further comprises:
a registering unit for registering the first image with the second image,
a local subtraction unit for locally subtracting the at least one high density element of the first image from the second image.

Since the first image has been reconstructed motion compensated using the determined motion in the small and large motion phases, the dimensions and the shape of the at least one high density element can be determined with a high reliability, which allows locally subtracting the at least one high density element of the first image from the second image with a high reliability resulting in a second image showing the contrast agent within the object in the region of interest with a reduced disturbance by the at least one high density element, in particular without being disturbed by the at least one high density element. The at least one high density element is preferentially a calcification of a heart comprising the contrast agent. Consequently, the quality of the image showing the contrast agent, for example, showing the vessels of a heart containing the contrast agent, is improved.

It is further preferred that the small motion determination unit is adapted for determining the motion of the object in the region of interest in the small motion phases from the second detection values,
wherein the large motion determination unit is adapted for determining the motion of the object in the region of interest in the large motion phases from the determined motion of the object, which has been determined from the second detection values, in the small motion phases,
wherein the reconstruction unit is adapted for reconstructing the second image of the region of interest from the second detection values, wherein the reconstruction unit is adapted for performing a motion compensation using the determined motions, which have been determined from the second detection values, in the small and large motion phases. Since also the second image is reconstructed motion compensated, the quality of the subtraction and, therefore, the quality of the final second image without the at least one high density element is further improved.

It is further preferred that the reconstruction unit is adapted for reconstructing the second image of the region of interest from the second detection values, wherein the reconstruction unit is adapted for performing a motion compensation using the determined motions, which have been determined from the first detection values, in the small and large motion phases. Since the motion, which has been determined for the first image, is used for a motion compensated reconstruction of the second image, the motion has to be determined only for the first image, thereby reducing the computational costs required for imaging the contrast agent within the object in the region of interest.

It is further preferred that the detection values provision unit is a detection values generation unit for generating first detection values, which depend on properties of the moving object, if the contrast agent is not present within the object, and for generating second detection values, which depend on properties of the moving object, if the contrast agent is present within the object.

In a further aspect of the present invention an imaging method for imaging a region of interest comprising a moving object, which moves less in small motion phases than in large motion phases, is presented, wherein the imaging method comprises following steps:

providing detection values, which depend on properties of the moving object,
determining the motion of the object in the region of interest in the small motion phases from the detection values,
determining the motion of the object in the region of interest in the large motion phases from the determined motion of the object in the small motion phases,
reconstructing an image of the region of interest from the detection values, wherein a motion compensation is performed using the determined motions in the small and large motion phases.

In a further aspect of the invention a motion determination method for determining the motion of a moving object, which moves less in small motion phases in a large motion phases, in a region of interest by a motion determination system, is presented, wherein the motion determination system is provided with detection values, which depend on properties of the moving object, wherein the motion determination method comprises following steps
determining the motion of the object in the region of interest in the small motion phases from the detection values by a small motion determination unit,
determining the motion of the object in the region of interest in the large motion phases from the determined motion of the object in the small motion phases by a large motion determination unit.

In a further aspect of the invention an imaging method for imaging a contrast agent within a moving object is presented, wherein the moving object comprises at least one high density element having a density within a given range of density in the region of interest and wherein the moving object moves less in small motion phases than in large motion phases, wherein the imaging method comprises following steps:
providing first detection values, which depend on properties of the moving object, if the contrast agent is not present within the object,
determining the motion of the object in the region of interest in the small motion phases from the first detection values,
determining the motion of the object in the region of interest in the large motion phases from the determined motion of the object in the small motion phases,
reconstructing a first image of the region of interest comprising the object comprising the at least one high density element from the first detection values, wherein a motion compensation is performed using the determined motions in the small and large motion phases,
providing second detection values, which depend on properties of at least one of the moving object and the contrast agent, if the contrast agent is present within the object,
reconstructing a second image of the region of interest of the object from the second detection values,
registering the first image with the second image,
locally subtracting the at least one high density element of the first image from the second image.

In a further aspect of the present invention a computer program for imaging a moving object is presented, wherein the computer program comprises program code means for causing a computer to carry out the steps of the method as claimed in claim 15 when the computer program is carried out on a computer controlling an imaging system as claimed in claim 1.

In a further aspect of the present invention a computer program for determining the motion of a moving object is presented, wherein the computer program comprises program code means for causing a computer to carry out the steps of the method as claimed in claim 16, when the computer program is carried out on a computer controlling a motion determination system as claimed in claim 9.

In a further aspect of the present invention a computer program for imaging a contrast agent within a moving object is presented, wherein the computer program comprises program code means for causing a computer to carry out the steps of the method as claimed in claim 17, when the computer program is carried out on a computer controlling an imaging system as claimed in claim 11.

It shall be understood that the imaging system for imaging a region of interest comprising a moving object of claim 1, the motion determination system for determining the motion of a moving object of claim 9, the imaging system for imaging a contrast agent within a moving object of claim 11, the imaging method for imaging a region of interest comprising a moving object of claim 15, the motion determination method for determining the motion of a moving object of claim 16, the imaging method for imaging a contrast agent within a moving object in a region of interest of claim 17, the computer program for imaging a region of interest comprising a moving object of claim 18, the computer program for determining the motion of a moving object in a region of interest of claim 19, and the computer program for imaging a contrast agent within a moving object in a region of interest of claim 20 have similar and/or identical preferred embodiments as defined in the dependent claims.

It shall be understood that preferred embodiments of the invention can also be a combination of, for example, two or more dependent claims with the respective independent claim.

BRIEF DESCRIPTION OF THE DRAWINGS

These and other aspect of the invention will be apparent from and elucidated with reference to the embodiments described hereinafter. In the following drawings

DETAILED DESCRIPTION OF EMBODIMENTS

Figure 1:
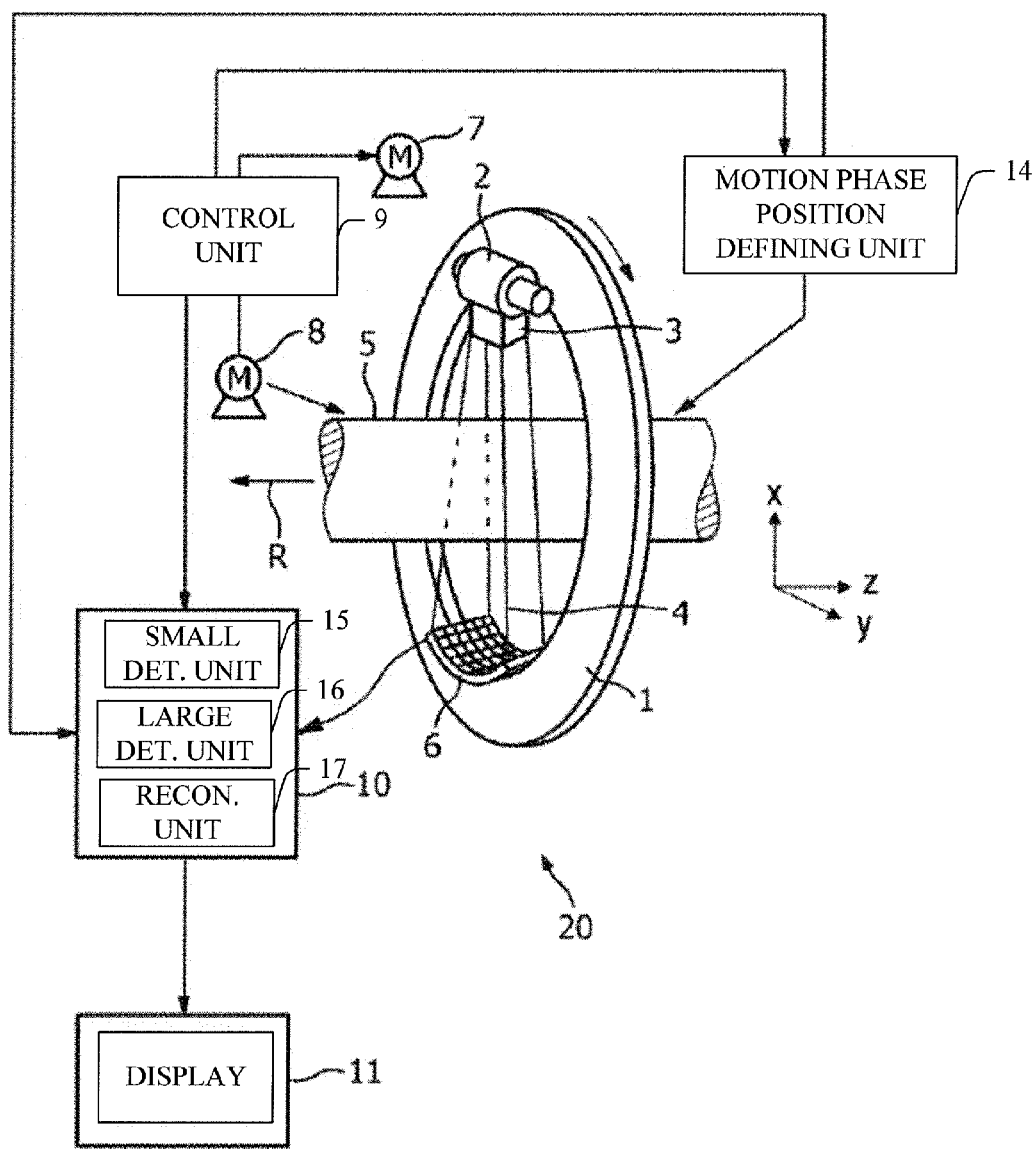
FIG. 1 shows schematically a representation of an imaging system for imaging a region of interest comprising a moving object in accordance with the invention.

FIG. 1. shows schematically an imaging system for imaging a region of interest comprising a moving object, which move less in small motion phases than in a large motion phases. This imaging system is, in this embodiment, a computed tomography system 20. The computed tomography system 20 includes a gantry 1, which is capable of rotating about an axis of rotation R which extends parallel to the z direction. A radiation source which is in this embodiment an X-ray source 2, is mounted on the gantry 1. The X-ray source 2 is provided with a collimator device 3, which forms a conical radiation beam 4 from the radiation emitted by the X-ray source 2. In other embodiments, the collimator 3 can be adapted for forming a radiation beam having another shape, for example, having a fan shape.

The radiation traverses a moving object (not shown), which move less in small motion phases than in a large motion phases and which is, for example, a heart of a patient or a moving technical object. The moving object is located in an examination zone 5. After having traversed the examination zone 5, the X-ray beam 4 is incident on a detection unit 6, in this embodiment a two-dimensional detector, which is mounted on the gantry 1. In other embodiments, the detection unit can also be a one-dimensional detector.

The gantry 1 is driven at a preferably constant, but adjustable angular speed by a motor 7. A further motor 8 is provided for displacing the examination zone 5, in which the moving object is located, parallel to the direction of the axis of radiation R or the z axis. The moving object is, for example, located on a moving table or conveyor belt, which are movable parallel to the direction of the axis of radiation R or the z axis by the motor 8. These motors 7, 8, the gantry 1, the X-ray source 2 and the detection unit 6 form a detection values generation unit for generating detection values which depend on properties of the moving object. The motors 7, 8 are controlled by a control unit 9 such that the radiation source 2 and the examination zone 5 move relative to each other along preferentially a circular or helical trajectory. For moving the X-ray source 2 and the examination zone 5 relative to each other along a circular trajectory, preferentially the X-ray source 2 is rotated and the examination zone 5 is not moved. For moving the X-ray source 2 and the examination zone 5 relative to each other along a helical trajectory, preferentially the X-ray source 2 is rotated and the examination zone 5 is moved parallel to the axis of rotation of R or the z axis.

The detection values acquired by the detection unit 6, i.e. the detection values generated by the detection values generation unit 1, 2, 6, 7, 8, are provided to a motion determination system 10 for determining the motion of the moving object and for reconstructing an image of a region of interest from the detection values, wherein a motion compensation is performed using the determined motion. The reconstructed image can finally be provided to a display 11 for displaying the generated image.

In another embodiment, in addition or alternatively, the reconstructed image of the region of interest can be provided to a calcium scoring unit, which performs a calcium scoring using the reconstructed image of the region of interest.

The motion determination system 10 comprises a small motion determination unit 15 for determining the motion of the object in the region of interest in small motion phases from the detection values, a large motion determination unit 16 for determining the motion of the object in the region of interest in the large motion phase from the determined motion of the object in the small motion phases and a reconstruction unit 17 for reconstructing an image of a region of interest from the detection values, wherein the reconstruction unit 17 is adapted for performing a motion compensation using determined motions in the small and large motion phases. Also the motion determination system 10 is preferably controlled by the control unit 9.

The computed tomography system 1 further comprises a motion phase position defining unit 14 for defining phase points within a motion cycle of a moving object, if the moving object is periodically moving as in this embodiment. The motion phase position defining unit 14 is, in this embodiment, an electrocardiograph for providing an electro-cardiogram, which is transmitted to the motion determination system 10. Also the motion phase position defining unit 14 is preferentially controlled by the control unit 9.

Figure 2:
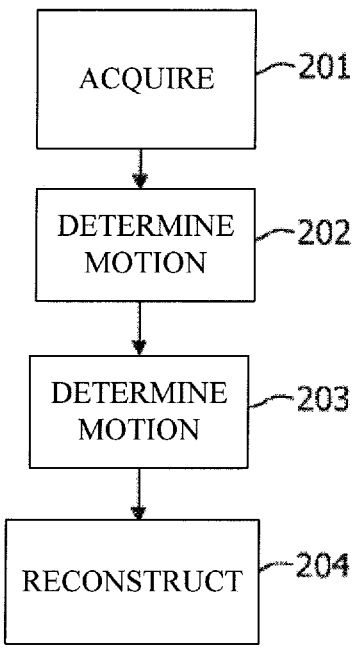
FIG. 2 shows a flow chart illustrating an embodiment of an imaging method for imaging a region of interest comprising a moving object in accordance with the invention.

In the following an imaging method for imaging a region of interest comprising a moving object, which moves less in small motion phases than in large motion phases, in accordance with the invention will be described in more detail with reference to a flow chart shown in FIG. 2.

In step 201, detection values are acquired by the detection unit 6, while the X-ray source 2 and the examination zone 5 move relative to each other along a circular trajectory, i.e. in this embodiment the X-ray source 2 is rotated and the moving table or the conveyor belt is not moved. The X-ray source 2 illuminates the moving object such that it is completely within a conical radiation beam 4 for each angular position of the X-ray source 2. In another embodiment, the X-ray source 2 and the examination zone 5 can move relative to each other along a helical trajectory. During the acquisition of the detection values the motion phase position defining unit 14, which is, in this embodiment, an electrocardiograph, records an electrocardiogram such that each detection value can be assigned to a motion phase position of the moving object.

Figure 3:
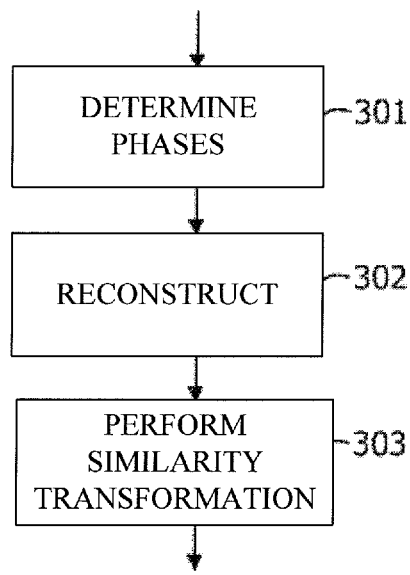
FIG. 3 shows a flow chart illustrating an embodiment of the determination of the motion of the object in a region of interest in a small motion phase in accordance with the invention.

The detection values and the corresponding determined motion phase positions are transmitted to the small motion determination unit 15, which determines the motion of the object in the region of interest in the small motion phases from the detection values in step 202. The determination of the motion of the object in the region of interest in the small motion phases from the detection values will now be described in more detail with reference to a flow chart shown in FIG. 3.

In step 301, the small motion phases and the large motion phases are determined. The small motion phases and the large motion phases are preferentially determined by reconstructing images of the region of interest at several phase positions defined by the motion phase point defining unit 14. This reconstruction can be performed by known gated reconstruction techniques. Images of adjacent phase positions are compared, for example, by applying a similarity measure, like a correlation or a sum of absolute differences, to these images, and if these images are similar with respect to the similarity measure, the motion of the object in the region of interest at these two phase points is a small motion, i.e. these two phase points belong to a small motion phase, and if the two images are not similar with respect to the similarity measure, the motion of the object at these two phase points is a large motion and these two phase points belong to a large motion phase. Two images are similar, if a similarity value resulting from a similarity measure applied to the two images is above a predetermined threshold. This threshold can be predetermined by calibration or experiments.

Preferentially, the motion map approach and/or local motion maps are used for determining the small motion phases and the large motion phases. In the motion map approach for determining location motion maps reconstructed images at adjacent phase points are compared within the region the interest, wherein the region of interest is preferentially a subvolume of an object, for example, a subvolume of a heart of a patient. The motion map approach for determining local motion maps is explained in more detail in "Automatic phase determination for retrospectively gated cardiac CT", Manzke et al., Med. Phys. 31 (12), December 2004, pp. 3345-3362, which is herewith incorporated by reference.

For the reconstruction of images of the region of interest at several motion phase positions a conventional cardiac CT reconstruction algorithm can be used, for example, aperture weighted cardiac reconstruction (AWCR), which is, for example, disclosed in "Aperture weighted cardiac reconstruction for cone-beam CT", Koken et al., Phys. Med. Biol. 51 (2006) 3433-3448, which is herewith incorporated by reference.

In step 302 images of the region of interest at several phase positions within the small motion phases are reconstructed from the detection values preferentially with a higher resolution and at more phase positions within a motion phase. Also for this reconstruction, a conventional cardiac CT reconstruction algorithm can be used, for example, AWCR.

In step 302 preferentially images of the region of interest are reconstructed at a number of phase positions preferentially in the range of 50 to 150 phase positions, further preferred in the range of 80 to 120 phase positions, and preferentially images of the region of interest are reconstructed at 100 different phase positions in step 302. In other embodiments, the images reconstructed in step 301 for determining the small motion phases and the large motion phases can also be used for determining the motion within the small motion phases in step 303, wherein, in this case, step 302 can be omitted.

In the following step 303, the motion of the object in the region of interest in the small motion phases, i.e. in this embodiment a motion vector field, is determined by comparing the images of the region of interest at the several phase positions in the respective small motion phase.

A motion vector field comprises for each voxel of the region of interest and for each phase position in a small motion phase, at which an image of the region of interest has been reconstructed, a motion vector, which describes the motion of the respective voxel from the position of the voxel at the respective phase position to a position of this voxel at the following phase position, at which an image of the region of interest has been reconstructed.

In step 303, for determining the motion from one phase position to another phase position within a small motion phase, a similarity transformation is determined such that a transformed image at the one phase position, to which the similarity transformation has been applied, is similar to the image at the other phase position with respect to a given similarity measure. Thus, in this embodiment, a similarity transformation is determined between each pair of neighbored phase positions within a small motion phase, at which images of the region of interest have been reconstructed in step 302 or, in another embodiment, in step 301. The determined similarity transformation of a small motion phase defines the movement of each voxel of the region of interest from one phase position to following phase positions and defines, therefore, the motion vector field of the small motion phase, i.e. the motion of the object in the region of interest in the small motion phase. The similarity transformation and, therefore, the motion vector fields are determined for several small motion phases, at least for two small motion phases.

The similarity transformation is determined by the small motion determination unit 15. The small motion determination unit 15 is preferentially adapted such that a similarity transformation between an image at one phase position and an image at another phase position is determined by firstly determining a translation such that an image of the region of interest, to which the translation has been applied, at the one phase position is similar to the image of the region of interest at the other phase position with respect to the given similarity measure, wherein the determined translation is used as initial similarity transformation for the determination of the similarity transformation.

The similarity transformation is preferentially a nine-parametric affine transformation. This nine-parametric affine transformation includes a translation, a rotation and a scaling. The similarity measure is preferentially a correlation or a sum of absolute differences. The similarity transformation between two phase positions within a small motion phase is preferentially determined by, as already mentioned above, firstly determining a translation and by using this translation as an initial similarity transformation for determining the final similarity transformation by using a down hill algorithm.

In another embodiment, in step 303, at least one high density element can be identified in the reconstructed images at the different phase positions in the respective small motion phase, and the similarity transformation can be determined such that a transformed at least one high density element, which is the at least high density element in the image at the one phase position, to which the similarity transformation has been applied, is similar to the at least one high density element in the image at the other phase position with respect to the given similarity measure. Also in this case, preferentially firstly a translation is determined as an initial similarity transformation of the determination of the final similarity transformation between two-phase positions within a small motion phase. Thus, in this embodiment, a motion vector field is determined only for voxels of the image of the region of interest, which show at least a part of the at least one high density element. Since these voxels can easily be identified in the different images at the different phase positions within a small motion phase and since not for all voxels of the region of interest, but only for the voxels of the region of interest, which show at least a part of the at least high density element, a motion vector field has to be determined, the motion vector field can determined with a high reliability and with reduced computational costs. Such a motion vector field is sufficient, if only the at least one high density element has to be reconstructed motion compensated. The at least one high density element is, for example, a calcification, wherein in each image of the images of the region of interest at the different phase positions within a small motion phase the voxels, which show at least a part of a calcification, can be determined by thresholding. A calcification is a high density element having a density preferentially in the range of 100 to 160 LU, further preferred in the range of 120 to 140 HU, and it is further preferred that the high density element has a density of 130 HU.

After the motion, i.e. the motion vector field in this embodiment, has been determined in step 202, i.e. in steps 301 to 303, the motion of the object within the region of interest in the large motion phase is determined from the motion of the object within the region of interest in the small motion phase, which has been determined in step 202, by the large motion determination unit 16 in step 203.

The large motion phases are located between small motion phases. Preferentially, the motion vector fields in the large phases are determined by interpolation using the determined motions, i.e. motion vector fields, of the small motion phases. It is further preferred that a spline interpolation is used for determining the motion vector fields in the large motion phases. In order to perform the interpolation, in this embodiment, firstly corresponding voxels in different small motion phases are identified by using a matching approach. After this identification and matching approach has been performed, the movement of a certain voxel within a region of interest is known in several different small motion phases. The interpolation can be performed in spatial space or in a parameter space defined by the parameters of the similarity transformation.

Figure 4:
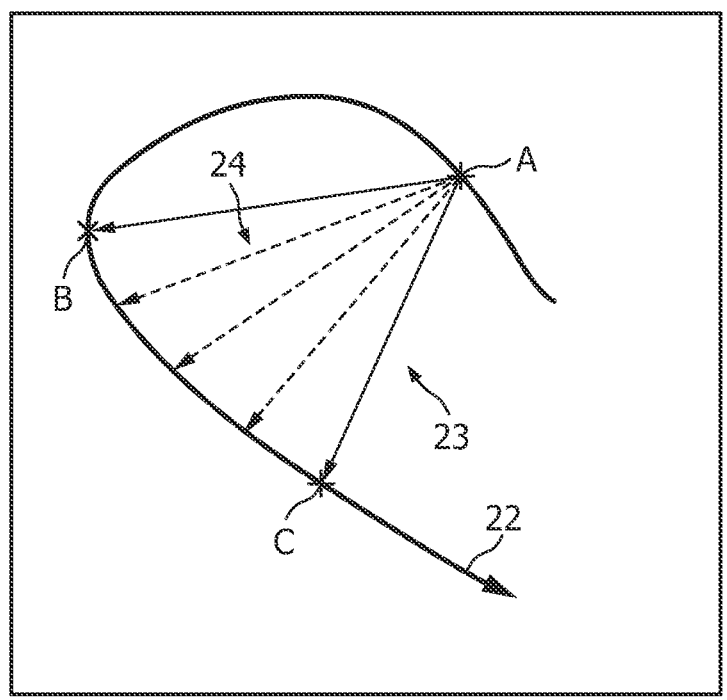
FIG. 4 shows schematically an interpolation for determining the motion of the object in the region of interest in a large motion phase from the determined motion of the object in small motion phases in a spatial space.

The interpolation in the spatial space is schematically shown in FIG. 4. FIG. 4 shows in the spatial space schematically a moving path 22, a long which a certain voxel moves. The movement of the voxel between the position A and the position B has been determined by determining the motion vector field of a small motion phase in step 202. Furthermore, the motion of the voxel after having passed the position C has also be determined in step 202 as the motion vector field of another small motion phase. The region between the positions B and C corresponds to a large motion phase, which is located between two neighbored small motion phases. The position of the voxel at the position B and at the position C is indicated by a cross and by solid line vectors 23 in FIG. 4. The motion of the voxel between these positions B and C, i.e. for example, the broken line vectors 24 in FIG. 4, is determined preferentially by a spline interpolation or a cubic interpolation.

The similarity transformation is determined between each two neighbored phase positions of a small motion phase, i.e. if 50 images have been reconstructed at 50 phase positions within a small motion phase, the similarity transformation defines 49 transformations between the images at the different phase positions. The resulting motion vector field describes the movement of a position of an element within the region of interest in the different images at the different phase positions within the small motion phase.

In step 204, a final image of the region of interest is reconstructed by the reconstruction unit 17 using a motion compensated reconstruction algorithm, wherein a motion compensation is performed using the determined motions, i.e. the determined motion vector fields in the small and large motion phases, and wherein the motion vector fields are related to reconstruction phase points for which motion compensated reconstruction can be applied.

The motion compensated reconstruction is well known and, for example, disclosed in "Motion-Compensated and Gated Cone Beam Filtered Back-Projection for 3-D Rotational X-Ray Angiography", Schaefer et al., IEEE TRANSACTIONS ON MEDICAL IMAGING, VOL. 25, NO. 7, JULY 2006, pp. 898-906, which is herewith incorporated by reference.

The region of interest comprises preferentially only one calcification of a heart of a patient. Therefore, the motion is determined for different calcifications, i.e. different regions of interest, independently from each other. This allows determining the motion within the region of interest independently from the motion of other parts of the heart yielding a high quality of the determined motion and, therefore, of the reconstructed and motion compensated image. Furthermore, since detection values, which correspond to large motion phases, can also be used for reconstruction, the signal-to-noise ratio is increased and motion artefacts are reduced or no more present.

Figure 5:
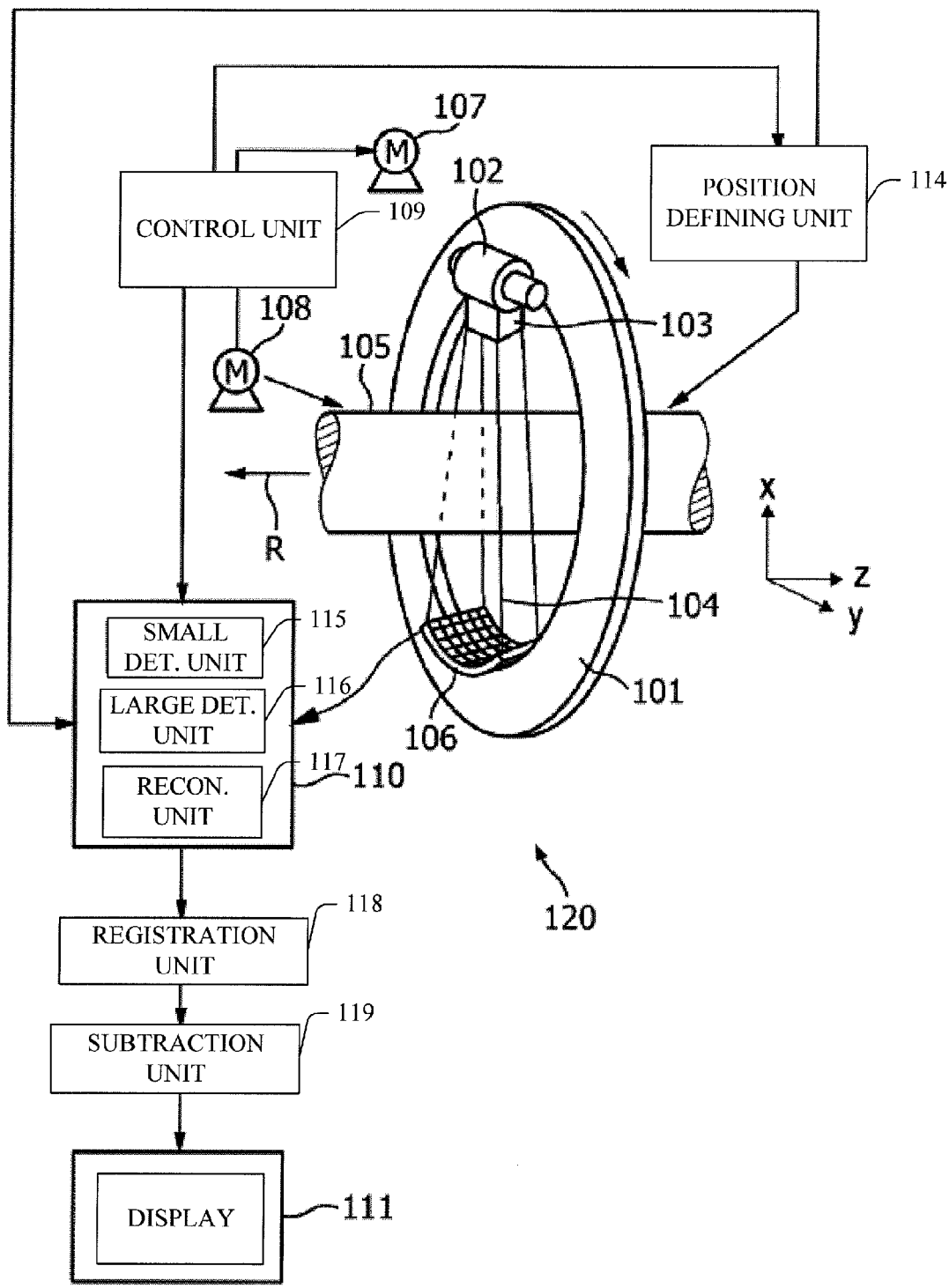
FIG. 5 shows schematically an embodiment of an imaging system for imaging a contrast agent within a moving object in a region of interest in accordance with the invention.

FIG. 5 shows schematically another imaging system 120 for imaging a contrast agent within a moving object in a region of interest. Also this imaging system is, in this embodiment, a computed tomography system. Similar to the imaging system 20 shown in FIG. 1, the imaging system 120 shown in FIG. 5 comprises a gantry 101, an X-ray source 102, a collimator device 103, a conical radiation beam 104, an examination zone 105, a detection unit 106, motors 107, 108, a control unit 109 and a motion phase position defining unit 114, which are similar to the corresponding units of the imaging system 20 shown in FIG. 1.

The moving object, in which a contrast agent has to be imaged, is a moving object, which comprises at least one high density element having a density within a given range of density of the region of interest and which moves less in small motion phases than in large motion phases. The object is, for example, a heart of a patient having calcifications as high density elements. The gantry 101, the X-ray source 102, the detection unit 106 and the motors 107, 108 are parts of a detection values provision unit. The detection values provision unit generates first detection values which depend on properties of the moving object, if the contrast agent is not present within the object. The imaging system 120 further comprises a motion determination system 110 including a small motion determination unit 115 for determining the motion of the object in the region of interest in the small motion phases from the first detection values, a large motion determination unit 117 for determining the motion of the object in the region of interest in the large motion phase from the determined motion of the object in the small motion phases and a reconstruction unit 116 for reconstructing a first image of the region of interest comprising the object, which comprises the at least high density element, from the first detection values, wherein the reconstruction 117 is adapted for performing a motion compensation using the determined motions in the small and large motion phases. Thus, from the first detection values a motion compensated image of the region of interest is reconstructed comprising the at least one high density element and not comprising the contrast agent.

The computed tomography system 120, in particular the detection values provision unit 101, 102, 106, 107, 108, is further adapted for providing second detection values which depend on properties of at least on of the moving object and a contrast agent, if the contrast agent is present within the object. The reconstruction unit 117 is further adapted for reconstructing a second image of the region of interest comprising the object from the second detection values.

The imaging system 120 further comprises a registration unit 118 for registering the first image with the second image, wherein preferentially the at least high density element is used for the registration, and a local subtraction unit 119 for locally subtracting the at least one high density element of the first image from the second image. The second image, from which the at least one high density element of the first image has been subtracted, can be displayed on the display 111.

Before the local subtraction, a second image shows the at least one high density element and the contrast agent within the region of interest and the first image shows the at least one high density element without the contrast agent. Thus, by locally subtracting the at least one high density element of the first image from the second image, after the local subtraction the second image shows the contrast agent within the region of interest substantially without the at least one high density element. If, for example, the moving object is a heart of a patient comprising a contrast agent for imaging coronary arteries and if the at least one high density element is a calcification, the imaging system 120 can provide an image of the contrast agent, i.e. of coronary arteries, with a reduced disturbance by calcifications, in particular without being disturbed by calcifications. Preferentially, the region of interest is dimensioned such that it comprises only one coronary artery of interest and a calcification. The imaging system 120 can image different regions of interest at different locations in the object, in particular in the heart of a patient, independently. This allows a high quality reconstruction of the contrast agent within the object, even if different parts of the object move differently.

Figure 6:
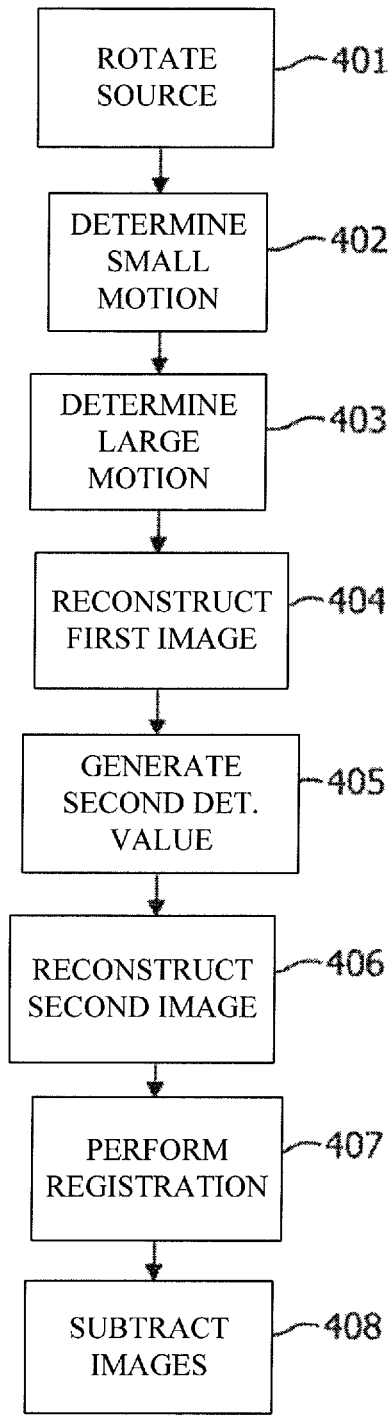
FIG. 6 shows a flow chart illustrating an embodiment of an imaging method for imaging a contrast agent within a moving object in a region of interest.

In the following an embodiment of an imaging method for imaging a contrast agent within a moving object in a region of interest, wherein the moving object comprises at least one high density element having a density within a given range of density in the region of interest and wherein the moving object moves less in small motion phases than in large motion phases, will be described with reference to a flow chart shown in FIG. 6.

In step 401, the X-ray source 102 rotates around the axis of rotation R or the z direction, and the object is not moved, i.e. the X-ray source 102 travels along a circular trajectory around the object. Preferentially, during the movement of the X-ray source 102 along the circular trajectory the object is always completely within the conical radiation beam 104. In another embodiment, the X-ray source 102 and the examination zone 105 can move along another trajectory relative to each other, for example, along a helical trajectory. The X-ray source 102 emits X-ray radiation traversing the object, in which a contrast agent is not present. The object is, for example, an organ of a patient, for example a heart of a patient, or a technical object. The X-ray radiation, which has passed the object, is detected by the detection unit 106, which generates first detection values, which depend on properties of the moving object.

In step 402, the small motion determination unit 115 determines the motion of the object in the region of interest in the small motion phases from the first detection values. This determination of the motion of the object in the region of interest is preferentially performed as described above with reference to step 202 in FIG. 2 and steps 301 to 303 in FIG. 3.

In step 403, the large motion determination unit 116 determines the motion of the object in the region of interest in the large motion phases from the determined motion of the object in the small motion phases, in particular by interpolation. Preferentially, this determination of the motion of the object in the region of interest in the large motion phases is performed as described above with reference to step 203 in FIG. 2.

The reconstruction unit 117 reconstructs the first image of the region of interest comprising the object, which comprises the at least one high density element, from the first detection values in step 404, wherein the reconstruction unit 117 performs a motion compensation using the motions in the small and large motion phases, determined in steps 402 and 403. This reconstruction is preferentially performed as described above with reference to step 204 in FIG. 2.

In step 405, the detection values provision unit 101, 102, 106, 107, 108 generates second detection values, wherein the X-ray source 102 and the examination zone move relative to each other as described above in step 401, i.e. the acquisition geometry and the movement of the X-ray source 102 with respect to the examination zone 105 is similar in steps 401 and 405. The difference between theses steps is that in step 401 a contrast agent is not present within the object and that in step 405 the contrast agent, for example, a gadolinium or iodine based contrast agent, is present within the object in a region of interest.

A second image of the object is reconstructed using the acquired second detection values by the reconstruction unit 117 in step 406. The second image can be reconstructed using a gated reconstruction technique, wherein, in this embodiment, an electrocardiogram of an electrocardiograph 114 is used, which is, in this embodiment, the motion phase position defining unit 114. Alternatively, also for reconstructing the second image, the motion within the small motion phases and the motion within the large motion phases can be determined from the second detection values as described above with reference to steps 202, 203 in FIG. 2 or with respect to steps 402 and 403 in FIG. 6, and these determined motions in the small motion phase and the large motion phase can be used for a motion compensated reconstruction also of the second image from the second detection values similar to the motion compensated reconstruction described above with reference to step 204 of FIG. 2 or step 404 of FIG. 6. In another embodiment, the motions of the moving object determined from the first detection values in steps 402 and 403 in the small motion phases and in the large motion phases can also be used for the motion compensated reconstruction of the second image from the second detection values in step 406, i.e. the motion determined from the first detection values can be used for the motion compensated reconstruction of the second image.

In step 407, the registration unit 118 registers the first image with respect to the second image, in particular, by registering voxels showing at least a part of the at least one high density element in the first and the second images.

In step 408, the at least one high density element, which can be identified by thresholding, of the first image is locally subtracted from the second image by the local subtraction unit 119. The second image, from which the at least one high density element of the first image has been locally subtracted, shows the contrast agent within the object in the region of interest with a reduced disturbance by the at least one high density element, in particular without being disturbed by the at least one high density element.

The moving object is preferentially a heart of a patient and the at least one high density element is preferentially a calcification. Furthermore, the region of interest is preferentially dimensioned such that it comprises one calcification. If a heart of a patient comprises several calcifications, preferentially the acquisition in steps 401 and 405 is performed one time, but the determination of the motions and the reconstructions in steps 402 to 404 and steps 406 to 408 is performed for each region of interest, i.e. for each calcification. Thus, the position and the shape of each calcification can be reconstructed and determined with a high reliability, and the calcifications shown in the first image can be subtracted from the respective second image yielding a high quality suppression of calcifications in the second images. Each second image shows preferentially a coronary artery of interest without being disturbed by a calcification.

The local subtraction is performed by subtracting the at least one high density element of the first image from the second image only in the voxels of the second image, which comprise at least a part of the at least one high density element, which is preferentially a calcification. When performing the local subtraction, the contrast disappears at the place where the calcification has been subtracted and the remaining lumen of the coronary artery remains. The local subtraction is explained in more detail in "Removal of arterial wall calcifications in CT angiography by local subtraction", M. van Straten et al., Med. Phys. 30 (5) 2003, pp. 761-770, which is herewith incorporated by reference.

In step 401 preferentially a calcium scoring scan and in step 405 preferentially a coronary angiography scan are performed. Furthermore, in steps 401 and 405 preferentially either a low pitch helical scan or a circular computed tomography scan with a large detector array enabling full object coverage over preferentially at least one cycle of the movement of the object, in particular over at least one heart beat, is performed. Thus, the object is preferentially a periodically moving object.

Preferentially, in step 406, a gated reconstruction of a coronary artery of interest is performed, in step 407 the calcification of the first image is preferentially registered to the second image, and step 408 a local subtraction is performed. Alternatively, preferentially in step 405 a set of gated reconstructions of a coronary artery of interest is performed, which is used for determining the motion of the coronary from the gated reconstructions, in particular as described above with respect step 402 in FIG. 6, steps 301 to 303 in FIG. 3 and step 202 in FIG. 2, and a motion compensated reconstruction of the coronary artery of interest is preferentially performed. Furthermore, in step 407 the calcification of the first image is preferentially registered to the calcification of second image showing the vessel structure of interest, and in step 408 a local subtraction is performed. In another embodiment, in step 406 the motion vector field determined for the movement of a calcification in the cardiac cycle in steps 402 and 403 is used to perform a motion compensated reconstruction of the coronary artery of interest containing the calcification. In this case, the calcification of the first image is registered to the calcification of the second image showing the vessel structure in step 407 and in step 408 a local subtraction is performed.

The above described local subtraction of calcifications of the first image from the second image showing the vessel structure reduces the effect of calcium blooming in coronary computed tomography angiography scans. If these coronary computed tomography angiography scans are used for an analysis of the vessel lumen, this vessel lumen analysis is improved.

In the following a further embodiment for determining the motion of a moving object, which moves less in small motion phases than in large motion phases, in a region of interest, is described, wherein it is assumed that the region of interest comprises tissue, calcifications and, if present, sharp transitions stemming from tissue to air.

Since calcifications, like bones, cause a strong attenuation of X-rays, they possess far greater CT-numbers than the surrounding tissue. Hence, calcified lesions provide a strong feature. Therefore, segmentation of calcified regions is preferentially done by thresholding followed by a region growing technique. The segmented calcifications are used to apply block matching. Block matching can be used to detect translative displacements. Hence, the largest calcification is segmented and framed serving as a block which is compared in another time frame.

The result is a displacement vector giving information about the translative part of the motion.

o achieve information about rotation and scaling of the object, the block matching algorithm uses a nine-parameter affine transformation model, which finds the best fit concerning translation, rotation and scaling via a multidimensional optimization of a similarity measure.

Motion vector fields are determined in the large motion phases by interpolation.

Interpolation between motion vector fields closes the gap between small motion phases.

Small and large motion phases are, in this embodiment, determined by determining a local motion map, which is a valuable method for determining small motion phases. The result is a similarity measure as a function of the phase point, in particular of the cardiac phase point. Within each small motion phase image registration can be applied. As image registration preferentially compares one image (template image) with another (target image), one image within each small motion phase is chosen to act as template. This image, for example the center image of each small motion phase, is referred to as Anchor Phase Point $P^{anchor}$ in the following. The small motion phases are chosen via consultation of the local motion map.

Image registration means an optimal fit between two images denoted, in this embodiment, as template and target image. The goal is to find those parameters, which describe optimally the transformation between the Anchor Phase Points $P_i^{anchor}$ of small motion phase i and phase points within the respective same small motion phase. The reconstructed template images have the intensity values $I(\vec{x}, P_i^{anchor})$ which are going to be matched onto target images having $I(\vec{x}, P)$. A preferred algorithm consists of three parts: Transformation Model, Cost Function, Optimization Algorithm.

For a given set of transformation parameters $$\vec{k} = (t_x, t_y, t_z, r_x, r_y, r_z, m_x, m_y, m_z)^T \quad (1)$$

a 3D image $I_{template}(\vec{x})$ is transformed. The ambition is to match this transformed image $I'_{template}(\vec{x})$ optimally onto the target-image $I_{target}(\vec{x})$. A cost function $c(\vec{k})$ is given by the measure of similarity. Thus, minimizing the cost leads to the optimal transformation parameters:

$$C_{template,target}(\vec{k}_{opt}) = \min[c_{template,target}(\vec{k})], \quad (2)$$

wherein minimizing is performed by varying $\vec{k}$.

Figure 7:
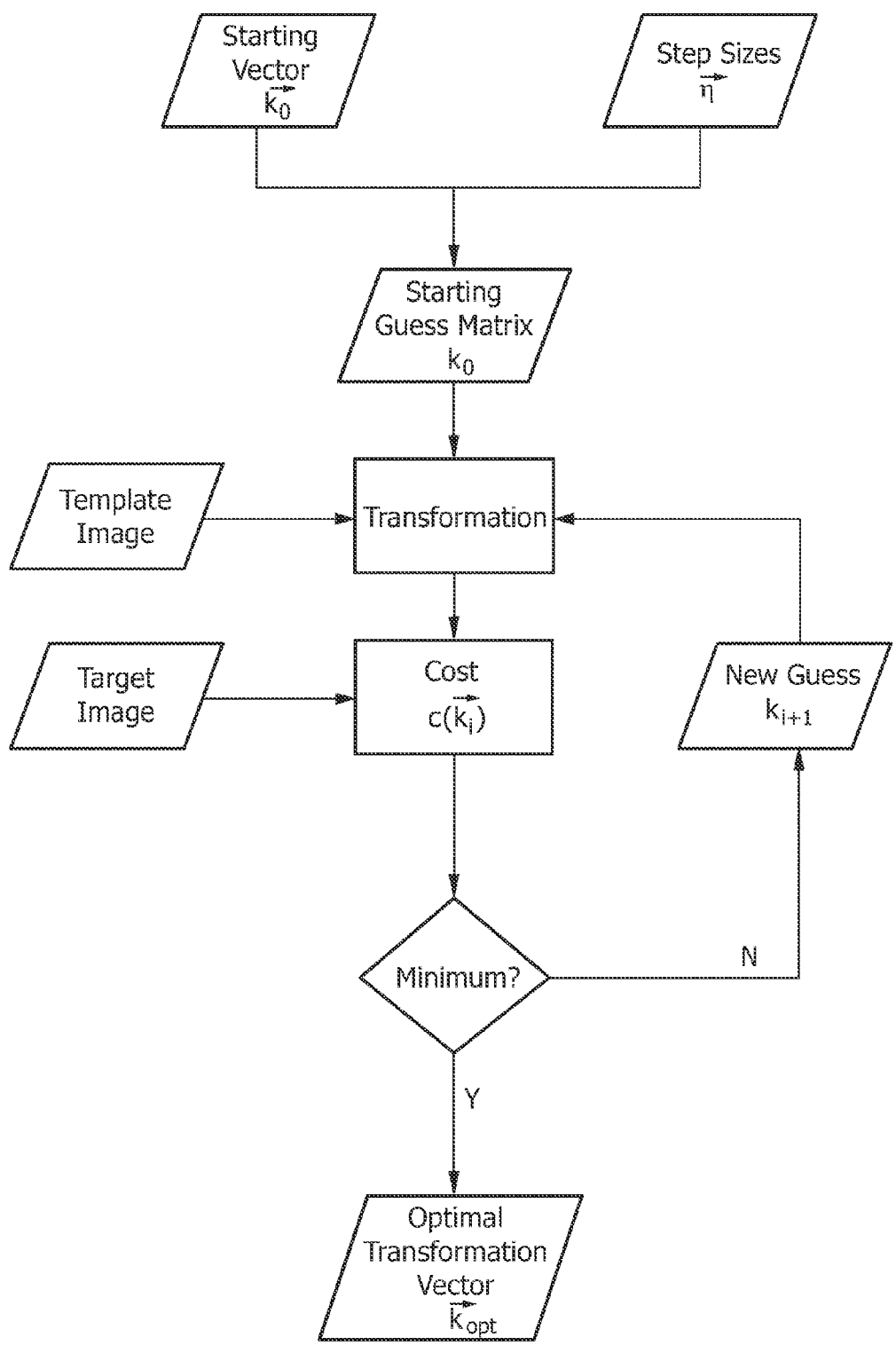
FIG. 7 shows a flow chart illustrating an embodiment of a determination of the motion of an object in a region of interest.

The strategy to find the optimal set of transformation parameters is depicted in FIG. 7.

In FIG. 7, a Downhill Simplex Algorithm is fed with a starting vector and a step-size vector, and a set of points in parameter space, which form the starting guess matrix $K_0$, is generated. The starting guess can be determined using an additional block matching algorithm. The cost function is a measure of the similarity between transformed template and target image.

Figure 8:
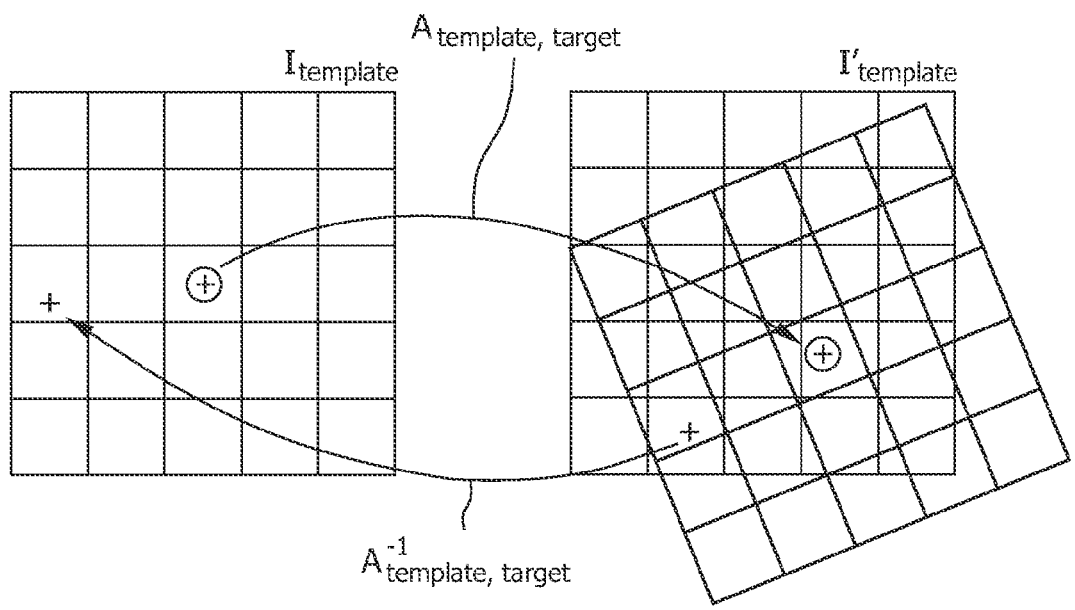
FIG. 8 shows schematically an affine transformation.

The transformation usually modifies the image in such a way that the voxels' centers do not match with the target's grid. Instead of projecting the template into the new frame, it is advantageous to calculate reversely the voxel values by applying the inverse matrix $A_{template,target}^{-1}$. As the center is surrounded by eight other voxels (except at the boundaries), these neighbors can be used to determine the intensity at the new centre's position (FIG. 8). Thus, it is appropriate to take a certain voxel of the transformed image and to calculate via the inverse matrix $A_{template,target}^{-1}$ its original position. In the original frame, the voxel's intensity can be calculated using interpolation schemes.

$$I'_{template}(\vec{x}) = I_{template,target}(A_{template,target}^{-1}(\vec{k}) \cdot \vec{x}) \quad (3)$$

Figure 9:
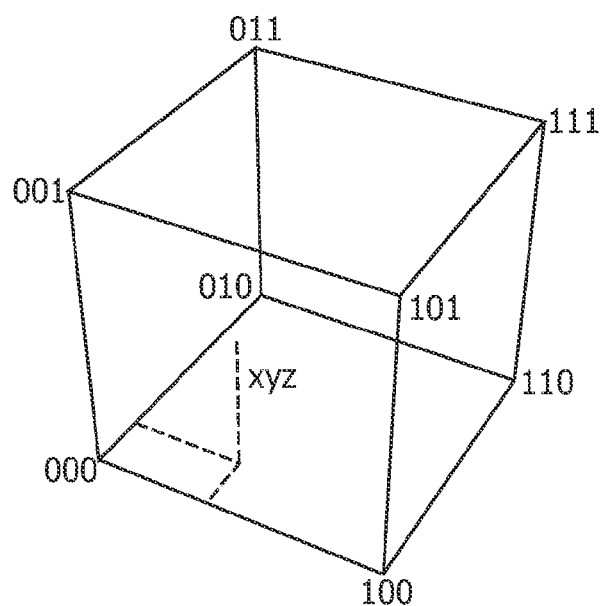
FIG. 9 shows a cuboid having assigned values to each corner.

Trilinear interpolation is a method to interpolate linearly points within a (cubic) box given values at the vertices. Consider a unit cube having assigned values to each corner as shown in FIG. 9. The values at each vertex are denoted $V_{ijk}$. The value at position (x, y, z) within the cube is determined by $$V_{xyz} = V_{000}(1-x)(1-y)(1-z) + V_{100}x(1-y)(1-z) + \\ V_{010}(1-x)y(1-z) + V_{001}(1-x)(1-y)z + \\ V_{101}x(1-y)z + V_{011}(1-x)yz + V_{110}xy(1-z) + V_{111}xyz \quad (4)$$

The cost function measures the similarity between $I'_{template}(\vec{x})$ and $I'_{target}(\vec{x})$. Thus, the value is determined by $$c(I'_{template}, I_{target}) = c(I_{template}, I_{target}, \vec{k}) \quad (5)$$

$$= c_{template,target}(\vec{k}) \quad (6)$$

Common cost functions for intra-modality similarity measures are mean squared differences, cross-correlation or the correlation-coefficient. The correlation-coefficient is not sensitive to changes in the amplitude of the compared images. The correlation-coefficient was implemented as cost function. The implemented optimization algorithm seeks for a minimum. Therefore, the function becomes:

$$c_{template,target}(\vec{k}) = \quad (7)$$

$$1 - \frac{\sum_{\vec{x} \in ROI} (I'_{template}(\vec{x}) - \overline{I'_{template}})(I_{target}(\vec{x}) - \overline{I_{target}})}{\left[\sum_{\vec{x} \in ROI} (I'_{template}(\vec{x}) - \overline{I'_{template}})^2 \sum_{\vec{x} \in ROI} (I_{target}(\vec{x}) - \overline{I_{target}})^2\right]^{\frac{1}{2}}}$$

where the overlined variables stand for mean values.

The last step in implementing an automated search for the best fit is preferentially an optimization algorithm, which seeks for the set of transformation parameters $\vec{k}^{opt}$. The first choice is the downhill simplex method. The task is an optimization problem in nine dimensions since the transformation incorporates translation, rotation and scaling in three dimensions, respectively.

A set of ten transformation guesses is preferentially made up in order to start the algorithm. Such a set can be established using one transformation vector and a step-size-vector which provides the edge-lengths $\vec{\eta}$.

An appropriate starting guess for the matching of images which inherit obviously little displacement, e.g. within small motion phases, can be the vector which does not transform the image:

$$\vec{k} = (0,0,0,0,0,0,1,1,1)^T \quad (8)$$

The second input is a step-size-vector $\vec{\eta}$. This vector creates a set of parameter-vectors which represent the vertices of the downhill simplex algorithm in parameter-space. They are of the size of typical length-scales of the single parameters. A meaningful choice is a step-size of a few millimeters, e.g. ±3 mm, for the translation-components $t_x$, $t_y$ and $t_z$, since the starting guess will provide a good first guess. Rotation and Scaling are considered to be moderate. Therefore, the step sizes for $r_x$, $r_y$ and $r_z$ are preferentially set to ±0.2(11.46°) and those for $m_x$, $m_y$ and $m_z$ preferentially to ±0.2.

In this embodiment, a local motion is supposed to be dominated by translation. Hence, an implemented block-matching algorithm should be able to deliver coarse information about the parameters $t_x$, $t_y$ and $t_z$. It can be used to run a full search prior to the downhill simplex algorithm in order to find a starting guess:

$$\vec{k} = (t_x, t_y, t_z, 0, 0, 0, 1, 1, 1)^T \quad (9)$$

To apply block matching, appropriate blocks are segmented within the template image. In the special case of tracking calcified areas, a cuboid frame around the largest calcification serves as search block. Calcifications are segmented using a threshold followed by a region growing algorithm. Then, this block is moved across the target image in order to find the best match. The gained transformation-information completes the starting vector in Eq (9). Finally, the starting guess is set up using this vector and the step-size-vector $\vec{\eta}$.

Up to this point, in this embodiment, motion vector fields for small motion phases have been calculated. This means, that we have obtained motion vector fields between the Anchor Phase Point and their neighbor phase points of each small motion phase, respectively.

The gathered motion information of each section is generally not connected to the other small motion phases. Thus, before interpolation all motion vector fields are preferentially related to one single phase point. Generally, every phase point of the small motion phases may be chosen as the reference phase point. To minimize the computational effort, one of the Anchor phase points can be chosen.

To translate a motion vector field from one small motion phase to the other, the motion vector field between the Anchor points $P_i^{anchor}$ or and the reference phase point, as mentioned above, e.g. the central Anchor phase point, $P_c^{anchor}$ is determined. Image registration is done between images of two (different) phase points. Let $A_{ij}$ be the matrix denoting the transformation from phase point $P_i$ to $P_j$ and $A_{ik}$ the transformation matrix belonging to the phase points $P_i$ and $P_k$:

$$\vec{x}_j = A_{ij} \vec{x}_i \quad (10)$$

$$\vec{x}_k = A_{ik} \vec{x}_i. \quad (11)$$

Using equation (10) and equation (11), one gets $$\vec{x}_k = A_{ik} A_{ij}^{-1} \vec{x}_j \quad (12)$$

and therefore $$A_{jk} = A_{ik} A_{ij}^{-1} \quad (13)$$

Figure 10:
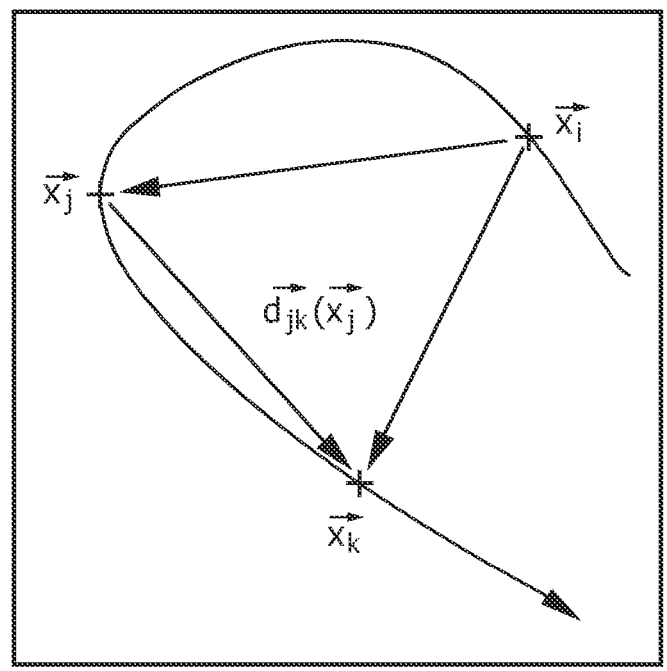
FIG. 10 shows schematically a shift of a reference point and FIG. 11 shows schematically an interpolation of the motion in large motion fields.

The displacement of $\vec{x}_j$ at phase point k is (see FIG. 10)

$$\vec{d}_{jk}(\vec{x}_j) = \vec{x}_k - \vec{x}_j. \quad (14)$$

Substitution of $\vec{x}_k$ with equations. (12) and (13) leads to $$\vec{d}_{jk}(\vec{x}_j) = A_{ik} A_{ij}^{-1} \vec{x}_j - \vec{x}_j \quad (15)$$

$$= (A_{jk} - I) \vec{x}_j, \quad (16)$$

wherein I is a 4×4 unity-matrix.

In this embodiment, in FIG. 10, to shift the reference point, it is necessary to possess both the motion vector $\vec{d}_{ij}$ from the old to the new reference point and $\vec{d}_{ik}$ denoting the motion vector from the old reference point to the phase point of interest.

Equation (13) describes the required calculations to propagate the motion vector field from phase point $P_i$ to $P_k$: If the motion vector field from one reference phase point $P_i^{ref}$ to a new reference phase point $P_j^{ref}$ is available and from $P_i^{ref}$ to $P_k$ as well, the motion vector field from $P_j^{ref}$ to $P_k$ can be calculated directly.

To estimate the motion for phase points of strong motion, i.e. in the large motion phases, interpolation is preferentially performed. There are two preferred methods to obtain interpolated motion vector fields: Interpolation in the spatial domain and interpolation in the parameter domain.

Interpolation in general is the estimation of values between a certain number of nodes. Several methods for interpolation can be used, such as linear interpolation, polynomial fits, cubic interpolation or bezier interpolation.

Interpolation in the spatial domain interpolates between $\vec{d}_{ci}(\vec{x}_c)$ for all phase points i and for all voxels $\vec{x}$ of the region of interest (ROI). Nodes for the interpolation are preferentially provided by $\vec{d}_{c,nodes}(\vec{x}_c)$ which are the displacement vectors for the voxels between $P_c^{anchor}$ and all phase points within the small motion phases. Interpolation in spatial domain space uses the estimated vectors of every single voxel for interpolation.

A second possibility is given for the interpolation of motion vector fields stemming from affine transformations. Since the parameters which generate the transformation matrix A are a function of time, a parameter interpolation can be done, denoted as interpolation in the parameter domain.

Figure 11:
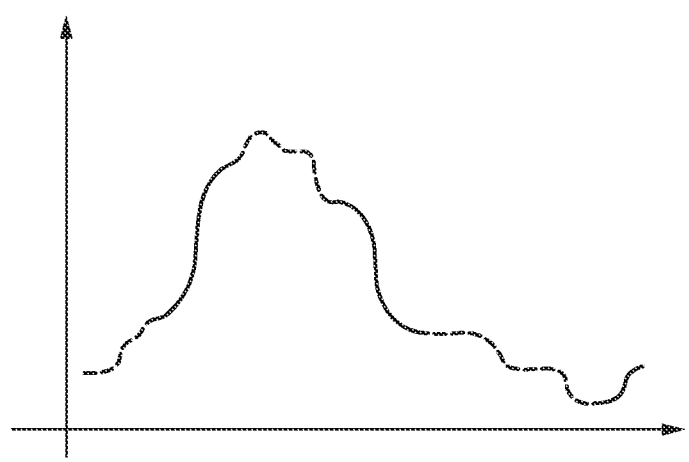

In FIG. 11, a parameter versus different phase points is shown. Transformation parameters are calculated in small motion phases (broken lines). Interpolation in parameter space uses the calculated transformation parameters for interpolation (solid lines).

The motion vector fields are related to reconstruction phase points for which motion compensated cardiac reconstruction can be applied.

While the invention has been illustrated and described in detail in the drawings and foregoing description, such illustration and description are to be considered illustrative or exemplary and not restrictive. The invention is not limited to the disclosed embodiments.

The imaging system can also comprise a memory as the detection values provision unit, in which the detection values, which have, for example, being acquired by a computed tomography system, and maybe also values of a motion phase position defining unit like an electrocardiograph are stored. Furthermore, the object can be a whole object or only a part of an object, and the object can also be a technical object or an organ, which is not the heart, for example, the object can be a renal artery. Moreover, in the above description with reference to FIG. 6, the acquisition of the second detection values, while a contrast agent is present within the object, can be performed before the acquisition of the first detection values, while the contrast agent is not present within the object. Furthermore, the reconstruction of the second image can also be performed before the reconstruction of the first image. Preferentially, the motion vector field is smoothed, in particular, if the motion vector field has shape bends.

Furthermore, the at least one high density element can have a density larger than the above mentioned 160 HU.

Other variations to the disclosed embodiments can be understood and effected by those skilled in the art and practicing the claimed invention from a study of the drawings, the disclosure and the appended claims.

In the claims, the word "comprising" does not exclude other elements or steps, and the indefinite article "a" or "an"

does not exclude a plurality. A single unit or other units may fulfill the functions of several items recited in the claims. One or several units, in particular their functions, can be implemented by one or several computer programs and/or by dedicated hardware. The mere fact that certain measures are recited in mutually different dependent claims does not indicate that the combination of these measures cannot be used to advantage.

A computer program may be stored/distributed on a suitable medium, such as an optical storage medium or a solid state medium supplied together with or as part of other hardware, but may also be distributed in other forms, such as via the internet or other wired or wireless telecommunication systems.

Any reference signs in the claims should not be construed as limiting the scope.

The invention claimed is:

1. An imaging system for imaging a region of interest comprising a moving object, which moves less in small motion phases than in large motion phases, wherein the imaging system comprises:
    a detection values provision unit for providing detection values, which depend on properties of the moving object,
    a small motion determination unit for determining the motion of the object in the region of interest in the small motion phases from the detection values,
    a large motion determination unit for determining the motion of the object in the region of interest in the large motion phases from the determined motion of the object in the small motion phases,
    a reconstruction unit for reconstructing an image of the region of interest from the detection values, wherein the reconstruction unit is adapted for performing a motion compensation using the determined motions in the small and large motion phases.

2. The imaging system as claimed in claim 1,
wherein the small motion determination unit is adapted for reconstructing images of the region of interest at several phase positions within the small motion phases from the detection values,
    determining the motion of the object in the region of interest in the small motion phases by comparing the images of the region of interest at the several phase positions.

3. The imaging system as claimed in claim 2,
wherein the small motion determination unit is adapted for
    determining the motion between one phase position to another phase position by determining a similarity transformation such that a transformed image at the one phase position, to which the similarity transformation has been applied, is similar to the image at the other phase position with respect to a given similarity measure,
    determining at least between two of the several phase points within a small motion phase at least one similarity transformation, wherein the at least one similarity transformation defines the motion within the small motion phase.

4. The imaging system as claimed in claim 3,
wherein the small motion determination unit is adapted for
    determining a similarity transformation between an image at one phase position and an image at another phase position by firstly determining a translation such that an image, to which the translation has been applied, at the one phase position is similar to the image at the other phase position with respect to the given similarity measure, wherein the determined translation is used as initial similarity transformation for the determination of the similarity transformation.

5. The imaging system as claimed in claim 2, wherein in the region of interest the object comprises at least one high density element having a density within a given density range and wherein the small motion determination unit is adapted for
    determining the motion between one phase position to another phase position by determining a similarity transformation such that a transformed at least one high density element, which is the at least high density element in the image at the one phase position, to which the similarity transformation has been applied, is similar to the at least one high density element in the image at the other phase position with respect to a given similarity measure,
    determining at least between two of the several phase points within a small motion phase at least one similarity transformation, wherein the at least one similarity transformation defines the motion within the small motion phase.

6. The imaging system as claimed in claim 5,
wherein the small motion determination unit is adapted for
    determining a similarity transformation between the at least one high density element in an image at one phase position and the at least one high density element in an image at another phase position by firstly determining a translation such that a translated at least one high density element, which is the at least high density element in the image at the one phase position, to which the translation has been applied, is similar to the at least one high density element in the image at the other phase position with respect to the given similarity measure, wherein the determined translation is used as initial similarity transformation for the determination of the similarity transformation.

7. The imaging system as claimed in claim 1,
wherein the large motion determination unit is adapted for
    determining the motion of the object in the region of interest in a large motion phase by interpolating between determined motions of small motion phases, which are adjacent to the large motion phase.

8. The imaging system as claimed in claim 1, wherein the detection values provision unit is a detection values generation unit for generating detection values, which depend on properties of the moving object.

9. A motion determination system for determining the motion of a moving object, which moves less in small motion phases than in large motion phases, in a region of interest, the motion determination system being provided with detection values, which depend on properties of the moving object, provided by a detection value provision unit, wherein the motion determination system comprises
    a small motion determination unit for determining the motion of the object in the region of interest in the small motion phases from the detection values,
    a large motion determination unit for determining the motion of the object in the region of interest in the large motion phases from the determined motion of the object in the small motion phases.

10. The motion determination system as claimed in claim 9,
    further comprising a reconstruction unit for reconstructing an image of the region of interest from the detection values, wherein the reconstruction unit is adapted for performing a motion compensation using the determined motions in the small and large motion phases.

11. An imaging system for imaging a contrast agent within a moving object in a region of interest, wherein the moving object comprises at least one high density element having a density within a given range of density in the region of interest and wherein the moving object moves less in small motion phases than in large motion phases, wherein the imaging system comprises:
- a detection values provision unit for providing first detection values, which depend on properties of the moving object, if the contrast agent is not present within the object,
- a small motion determination unit for determining the motion of the object in the region of interest in the small motion phases from the first detection values,
- a large motion determination unit for determining the motion of the object in the region of interest in the large motion phases from the determined motion of the object in the small motion phases,
- a reconstruction unit for reconstructing a first image of the region of interest comprising the object comprising the at least one high density element from the first detection values, wherein the reconstruction unit is adapted for performing a motion compensation using the determined motions in the small and large motion phases,
- wherein the detection values provision unit is further adapted for providing second detection values, which depend on properties of at least one of the moving object and the contrast agent, if the contrast agent is present within the object, and
- wherein the reconstruction unit is further adapted for reconstructing a second image of the region of interest comprising the object from the second detection values,
- wherein the imaging system further comprises:
- a registering unit for registering the first image with the second image,
- a local subtraction unit for locally subtracting the at least one high density element of the first image from the second image.

12. The imaging system as claimed in claim 11,
- wherein the small motion determination unit is adapted for determining the motion of the object in the region of interest in the small motion phases from the second detection values,
- wherein the large motion determination unit is adapted for determining the motion of the object in the region of interest in the large motion phases from the determined motion of the object, which has been determined from the second detection values, in the small motion phases,
- wherein the reconstruction unit is adapted for reconstructing the second image of the region of interest from the second detection values, wherein the reconstruction unit is adapted for performing a motion compensation using the determined motions, which have been determined from the second detection values, in the small and large motion phases.

13. The imaging system as claimed in claim 12,
- wherein the reconstruction unit is adapted for reconstructing the second image of the region of interest from the second detection values, wherein the reconstruction unit is adapted for performing a motion compensation using the determined motions, which have been determined from the first detection values, in the small and large motion phases.

14. The imaging system as claimed in claim 11, wherein the detection values provision unit is a detection values generation unit for generating first detection values, which depend on properties of the moving object, if the contrast agent is not present within the object, and for generating second detection values, which depend on properties of the moving object, if the contrast agent is present within the object.

15. An imaging method for imaging a region of interest comprising a moving object, which moves less in small motion phases than in large motion phases, wherein the imaging method comprises following steps:
- providing detection values, which depend on properties of the moving object,
- determining the motion of the object in the region of interest in the small motion phases from the detection values,
- determining the motion of the object in the region of interest in the large motion phases from the determined motion of the object in the small motion phases,
- reconstructing an image of the region of interest from the detection values, wherein a motion compensation is performed using the determined motions in the small and large motion phases.

16. A motion determination method for determining the motion of a moving object, which moves less in small motion phases than in large motion phases, in a region of interest by a motion determination system, the motion determination system being provided with detection values, which depend on properties of the moving object, wherein the motion determination method comprises following steps
- determining the motion of the object in the region of interest in the small motion phases from the detection values by a small motion determination unit,
- determining the motion of the object in the region of interest in the large motion phases from the determined motion of the object in the small motion phases by a large motion determination unit.

17. An imaging method for imaging a contrast agent within a moving object in a region of interest, wherein the moving object comprises at least one high density element having a density within a given range of density in the region of interest and wherein the moving object moves less in small motion phases than in large motion phases, wherein the imaging method comprises following steps:
- providing first detection values, which depend on properties of the moving object, if the contrast agent is not present within the object,
- determining the motion of the object in the region of interest in the small motion phases from the first detection values,
- determining the motion of the object in the region of interest in the large motion phases from the determined motion of the object in the small motion phases,
- reconstructing a first image of the region of interest comprising the object comprising the at least one high density element from the first detection values, wherein a motion compensation is performed using the determined motions in the small and large motion phases,
- providing second detection values, which depend on properties of at least one of the moving object and the contrast agent, if the contrast agent is present within the object,
- reconstructing a second image of the region of interest of the object from the second detection values,
- registering the first image with the second image,
- locally subtracting the at least one high density element of the first image from the second image.

18. A computer program residing on a non-transitory computer readable medium for imaging a region of interest comprising a moving object, comprising program code means for causing a computer to carry out the steps of the method as claimed in claim 15.

19. A computer program residing on a non-transitory computer readable medium for determining the motion of a moving object in a region of interest, comprising program code means for causing a computer to carry out the steps of the method as claimed in claim 16.

20. A computer program residing on a non-transitory computer readable medium for imaging a contrast agent within a moving object in a region of interest, comprising program code means for causing a computer to carry out the steps of the method as claimed in claim 17.

* * * * *